(12) United States Patent
Pagan et al.

(10) Patent No.: US 9,976,953 B2
(45) Date of Patent: *May 22, 2018

(54) OPTICAL DENSITY MONITOR AND COMPARATOR SYSTEMS AND METHODS

(71) Applicants: The University of North Carolina at Charlotte, Charlotte, NC (US); AquiSense Technologies LLC, Walton, KY (US)

(72) Inventors: Jennifer Godwin Pagan, Charlotte, NC (US); Edward Brittain Stokes, Charlotte, NC (US); Paolo Batoni, Charlotte, NC (US)

(73) Assignees: AquiSense Technologies LLC, Erlanger, KY (US); The University of North Carolina at Charlotte, Charlotte, NC (US)

(*) Notice: Subject to any disclaimer, the term of this patent is extended or adjusted under 35 U.S.C. 154(b) by 470 days.

This patent is subject to a terminal disclaimer.

(21) Appl. No.: 14/271,859

(22) Filed: May 7, 2014

(65) Prior Publication Data
US 2014/0240695 A1    Aug. 28, 2014

Related U.S. Application Data

(63) Continuation-in-part of application No. 13/163,055, filed on Jun. 17, 2011, and a continuation of
(Continued)

(51) Int. Cl.
*G01N 21/59* (2006.01)
*A61L 9/20* (2006.01)
(Continued)

(52) U.S. Cl.
CPC .......... *G01N 21/5907* (2013.01); *A61L 9/205* (2013.01); *G01N 21/031* (2013.01);
(Continued)

(58) Field of Classification Search
CPC ... A61L 9/20; A61L 9/205; A61L 2/10; A61L 2209/11; C02F 1/32; C02F 1/325;
(Continued)

(56) References Cited

U.S. PATENT DOCUMENTS

| 5,874,741 A | 2/1999 | Matschke |
| 6,118,134 A * | 9/2000 | Justak ................... G01F 23/292 |
| | | 250/574 |

(Continued)

FOREIGN PATENT DOCUMENTS

| EP | 1843401 A1 | 10/2007 |
| EP | 1887297 A1 | 2/2008 |
| WO | WO2009021108 A1 | 2/2009 |

OTHER PUBLICATIONS

Linden, Karl, et al., "Ultraviolet disinfection of marginal effluents: determining ultraviolet absorbance and subsequent estimation of ultraviolet intensity," 1998, Water Environment Research, vol. 70, No. 2, 214-223, 10 pages.*

(Continued)

*Primary Examiner* — Patrick J Orme
(74) *Attorney, Agent, or Firm* — Hasse & Nesbitt LLC; Donald E. Hasse

(57) ABSTRACT

The present disclosure relates generally to systems and methods for determining the absorption coefficient and the optical density of a fluid as they relate to the wavelength of incident radiation. Specifically, ultraviolet light-emitting diodes (UV LEDs) or the like that emit ultraviolet (UV) radiation or the like are used as sources for irradiating the interior of an integrating chamber that is designed to increase the path length of the radiation through the fluid, thus enhancing the detection limits of the absorption coefficient and the optical density according to Beer's Law.

16 Claims, 4 Drawing Sheets

Related U.S. Application Data application No. PCT/US2009/068765, filed on Dec. 18, 2009.

(60) Provisional application No. 61/820,204, filed on May 7, 2012, provisional application No. 61/139,022, filed on Dec. 19, 2008.

(51) Int. Cl.
  *G01N 21/03* (2006.01)
  *G01N 21/33* (2006.01)
  *C02F 1/32* (2006.01)

(52) U.S. Cl.
  CPC .......... *G01N 21/33* (2013.01); *A61L 2209/11* (2013.01); *C02F 1/32* (2013.01); *C02F 2209/11* (2013.01); *C02F 2303/04* (2013.01); *G01N 2201/065* (2013.01)

(58) Field of Classification Search
  CPC ...... C02F 2201/3222; C02F 2201/3227; C02F 2201/3228; C02F 2303/04; C02F 2209/11; G01N 21/03; G01N 21/33; G01N 2201/065; G01N 21/031; G01N 21/5907
  See application file for complete search history.

(56) References Cited

U.S. PATENT DOCUMENTS

| | | | |
|---|---|---|---|
| 6,555,011 B1 * | 4/2003 | Tribelsky | A61L 2/08 204/158.2 |
| 7,554,109 B2 | 6/2009 | Stokes | |
| 2003/0194692 A1 | 10/2003 | Purdum | |
| 2005/0274663 A1 | 12/2005 | Roitman | |
| 2007/0081155 A1 * | 4/2007 | Schembri | B01L 3/0275 356/246 |
| 2009/0269868 A1 | 10/2009 | Stokes | |
| 2012/0318749 A1 * | 12/2012 | Stokes | C02F 1/325 210/748.09 |
| 2014/0161664 A1 | 6/2014 | Harris et al. | |
| 2014/0240695 A1 | 8/2014 | Pagan et al. | |

OTHER PUBLICATIONS

Goebel, "Generalized Integrating-Sphere Theory", Applied Optics, Jan. 1967, pp. 125-128, 6(1).
Karagodsky et al., "Theoreticai Analysis of Subwavelength High Contrast Grating Reflectors", Optics Express, Jul. 26, 2010, pp. 16973-16988, 18(16).
Rode, Gaddam and Yi, "Subnanometer surface roughness of dc Magnetron Puttered Al films", J. Appl. Phys., 2007, pp, 024303-1-0243038, 102.
Ocean Optics, WS-1 Reflectance Standards, http://oceanoptics.com/product/ws-1-refectance-standards/.
Fry, Katatwar, and Pope, "Integrating Cavity Absorption Meter", Applied Optics, Apr. 20, 1992, pp. 2055-2065, 31(12).
Elterman, "Integrative Cavity Spectroscopy", Applied Optics, Sep. 1970, pp. 2140-2142, 9(9).
Goebel, "Generalized Integrating-Sphere Theory", Applied Optics, Jan. 1967, pp. 125-128, 6(1).
Winston, Minano, Benitez, "Nonimaging Optics", Elsevier Academic Press, 2005, Chapter 4.1 Limits to Concentration.
Karagodsky et al., "Theoretical Analysis of Subwavelength High Contrast Grating Reflectors", Optics Express, Jul. 26, 2010, pp. 16973-16988, 18(16).
Frear et al., "Structure and Properties of Al-1%Si Thin Films on Si as a Function of Gas Inpurities During DC Magnetron-Sputtered Deposition", Journal of Electronic Materials, 1989, pp. 517-525, 18(4).
Rode, Gaddam and Yi, "Subnanometer surface roughness of dc Magnetron Puttered Al films", J. Appl. Phys., 2007, pp. 024303-1-0243038, 102.
Ocean Optics, STAN Series Reflectance Standards, http://oceanoptics.com/product/stan-series-refectance-standards/.
Ocean Optics, WS-1 Reflectance Standards, http://oceanoptics.com/products/ws-1-refectance-standards/.
Wladyslaw Kowalski, "Ultraviolet Germicidal Irradiation Handbook", Appendix F: Ultraviolet Material Reflectivities (UVC/UVB Range), Springer, p. 491.
Javorfi, Tamas, et al., "Quantitative spectrophotometry using integrating cavities", 2006, J. of Photochemistry & photobiology B: Biology, 82, pp. 127-131.

* cited by examiner

OPTICAL DENSITY MONITOR AND COMPARATOR SYSTEMS AND METHODS

CROSS-REFERENCE TO RELATED APPLICATION

The present patent application/patent is a continuation-in-part of co-pending U.S. patent application Ser. No. 13/163,055, filed on Jun. 17, 2011, and entitled "SYSTEMS AND METHODS FOR PERFORMING THE BACTERIAL DISINFECTION OF A FLUID USING POINT RADIATION SOURCES," which is a continuation of Patent Cooperation Treaty (PCT) Patent Application No. PCT/US09/68765, filed on Dec. 18, 2009, and entitled "SYSTEMS AND METHODS FOR PERFORMING THE BACTERIAL DISINFECTION OF A FLUID USING POINT RADIATION SOURCES," which claims the benefit of priority of U.S. Provisional Patent Application No. 61/139,022, filed on Dec. 19, 2008, and entitled "BACTERIAL DISINFECTION UNIT," the contents of all of which are incorporated in full by reference herein. The present patent application/patent also claims the benefit of priority of U.S. Provisional Patent Application No. 61/820,204, filed on May 7, 2013, and entitled "OPTICAL DENSITY MONITOR AND COMPARATOR," the contents of which are incorporated in full by reference herein.

STATEMENT REGARDING FEDERALLY SPONSORED RESEARCH OR DEVELOPMENT

The U.S. Government may have certain rights in the present disclosure pursuant to Award Nos. 0740524 and 0848759 by the National Science Foundation (NSF).

FIELD OF THE DISCLOSURE

The present disclosure relates generally to systems and methods for determining the absorption coefficient and the optical density of a fluid as they relate to the wavelength of incident radiation. Specifically, ultraviolet light-emitting diodes (UV LEDs) or the like that emit ultraviolet (UV) radiation or the like are used as sources for irradiating the interior of an integrating chamber that is designed to increase the path length of the radiation through the fluid, thus enhancing the detection limits of the absorption coefficient and the optical density according to Beer's Law.

BACKGROUND OF THE DISCLOSURE

The use of integrating spheres or multi-pass cells for quantifying the optical density of a fluid is prolific; however, in most of these applications, the fluid being examined is disposed in a sample container (e.g. a cuvette) and placed inside or against a porthole manufactured in the side of the sphere of cell. A radiation source, typically a halogen, mercury, or deuterium lamp, is used to irradiate the fluid inside the sample container. Some light is absorbed by the fluid and the remainder is scattered into the interior of the sphere or cell. After being multiply scattered, the remaining light exits the sphere or cell through a porthole and is detected by a spectrometer or the like. The path length in this type of measurement is determined by the dimensions of the cuvette, and is not enhanced by multiple scattering inside the sphere or cell. This is a common methodology in the field of absorption spectroscopy, where the amount of light absorbed can be correlated to the concentration of a molecule in the fluid. In this methodology, attenuation due to light absorption can be separated from attenuation due to light scattering through the integrating sphere or multi-pass cell; however, there is no enhancement of absorption coefficient measurement, as the path length is determined strictly by the cuvette dimensions. Thus, what are still needed in the art are improved systems and methods for determining the absorption coefficient and the optical density of a fluid as they relate to the wavelength of incident radiation.

Further, nucleic acid quantitation is used prolifically to determine the presence and the concentration of deoxyribonucleic acid (DNA) and ribonucleic acid (RNA) in a sample. There are several methodologies used to measure such concentrations. When relatively low concentrations of DNA are present, fluorescent dyes are used that bind to the nucleic acid and the resulting fluorescent intensity is compared to control samples. This method can be more time consuming than other methods, but is more accurate at relatively low sample concentrations. The Slot-Blot technique can also be used for relatively low sample concentrations, but requires adding a hybridizing agent and relies on luminescence measurement. Absorption spectroscopy is a commonly used method whereby the sample absorbance at 260 nm is correlated to the concentration and the sample absorbance at 280 nm. It may also be used to ascertain sample purity or contamination of a protein sample by DNA as compared to the 260 nm absorption. This method is defined by the Beer-Lambert Law, where absorption is a function of the path length of the sample. Because, as described above, the samples of interest are typically in held small cuvettes (i.e. about 1-cm path length) or microplates, they must have sufficient DNA concentrations to allow for measurement, or, be mechanically concentrated prior to sampling (as required for a nanodrop spectrophotometer). If the path length of the sample can be increased, then the level of sensitivity of the measurement can be increased; alternatively, smaller sample volumes can be used for measurement. Thus, what are still needed in the art are improved systems and methods for determining the presence and the concentration of DNA and RNA in a sample by exploiting increased path length.

BRIEF SUMMARY OF THE DISCLOSURE

In various exemplary embodiments, the present disclosure provides an integrating sphere or multi-pass cell (collectively referred to herein as a flow cell) including one or more UV LEDs or the like disposed around the interior periphery thereof. The one or more UV LEDs are operable for irradiating the interior of the flow cell, which contains and confines a fluid sample in substantially the entire internal volume of the flow cell, thereby maximizing path length through the fluid sample. A detector is also disposed at the interior periphery of the flow cell, such that scattered radiation within the interior of the flow cell impinges on and is detected by the detector.

In one exemplary embodiment, the present disclosure provides a system for determining the absorption coefficient and/or the optical density of a fluid, including: an integrating flow cell configured to contain a fluid sample within substantially an entire interior portion thereof; one or more point radiation sources disposed about an interior periphery of the integrating flow cell, wherein the one or more point radiation sources are operable for delivering radiation of a predetermined wavelength to the fluid sample; and one or more radiation detectors operable for detecting radiation within the interior portion of the integrating flow cell; wherein an interior surface of the integrating flow cell is operable for reflecting the radiation delivered to the fluid sample by the one or more point radiation sources; and wherein a path length of the radiation delivered to the fluid sample and reflected is maximized by the fluid sample occupying substantially the entire interior portion of the integrating flow cell. The absorption coefficient and/or the optical density of the fluid is determined utilizing the predetermined wavelength of the delivered radiation and a characteristic (e.g. intensity) of the detected radiation. The integrating flow cell includes one or more of an integrating cavity, an integrating ellipsoid, an integrating sphere, and a multi-pass cell. Preferably, the one or more point radiation sources include a first point radiation source operable for delivering radiation of a first predetermined wavelength to the fluid sample. Optionally, the one or more point radiation sources further include a second point radiation source operable for delivering radiation of a second predetermined wavelength to the fluid sample. Optionally, the one or more point radiation sources include one or more UV point radiation sources. Optionally, the one or more point radiation sources include a point radiation source operable for delivering radiation having a predetermined wavelength of between about 260 nm and about 280 nm to the fluid sample. The interior surface of the integrating flow cell is operable for reflecting the radiation delivered to the fluid sample by the one or more point radiation sources such that a radiation intensity is uniform throughout the interior portion of the integrating flow cell. Optionally, the system also includes an algorithm operable for quantifying a degree of disinfection of the fluid sample using the detected radiation. Alternatively, the system includes an algorithm operable for quantifying nucleic acids in the fluid sample using the detected radiation.

In another exemplary embodiment, the present disclosure provides a method for determining the absorption coefficient and/or the optical density of a fluid, including: providing an integrating flow cell configured to contain a fluid sample within substantially an entire interior portion thereof; providing one or more point radiation sources disposed about an interior periphery of the integrating flow cell, wherein the one or more point radiation sources are operable for delivering radiation of a predetermined wavelength to the fluid sample; and providing one or more radiation detectors operable for detecting radiation within the interior portion of the integrating flow cell; wherein an interior surface of the integrating flow cell is operable for reflecting the radiation delivered to the fluid sample by the one or more point radiation sources; and wherein a path length of the radiation delivered to the fluid sample and reflected is maximized by the fluid sample occupying substantially the entire interior portion of the integrating flow cell. The absorption coefficient and/or the optical density of the fluid is determined utilizing the predetermined wavelength of the delivered radiation and a characteristic (e.g. intensity) of the detected radiation. The integrating flow cell includes one or more of an integrating cavity, an integrating ellipsoid, an integrating sphere, and a multi-pass cell. Preferably, the one or more point radiation sources include a first point radiation source operable for delivering radiation of a first predetermined wavelength to the fluid sample. Optionally, the one or more point radiation sources further include a second point radiation source operable for delivering radiation of a second predetermined wavelength to the fluid sample. Optionally, the one or more point radiation sources include one or more UV point radiation sources. Optionally, the one or more point radiation sources include a point radiation source operable for delivering radiation having a predetermined wavelength of between about 260 nm and about 280 nm to the fluid sample. The interior surface of the integrating flow cell is operable for reflecting the radiation delivered to the fluid sample by the one or more point radiation sources such that a radiation intensity is uniform throughout the interior portion of the integrating flow cell. Optionally, the method also includes providing an algorithm operable for quantifying a degree of disinfection of the fluid sample using the detected radiation. Alternatively, the method includes providing an algorithm operable for quantifying nucleic acids in the fluid sample using the detected radiation.

BRIEF DESCRIPTION OF THE DRAWINGS

The present disclosure is illustrated and described herein with reference to the various drawings, in which like reference numbers are used to denote like system components/method steps, as appropriate, and in which.

DETAILED DESCRIPTION OF THE DISCLOSURE

Figure 1:
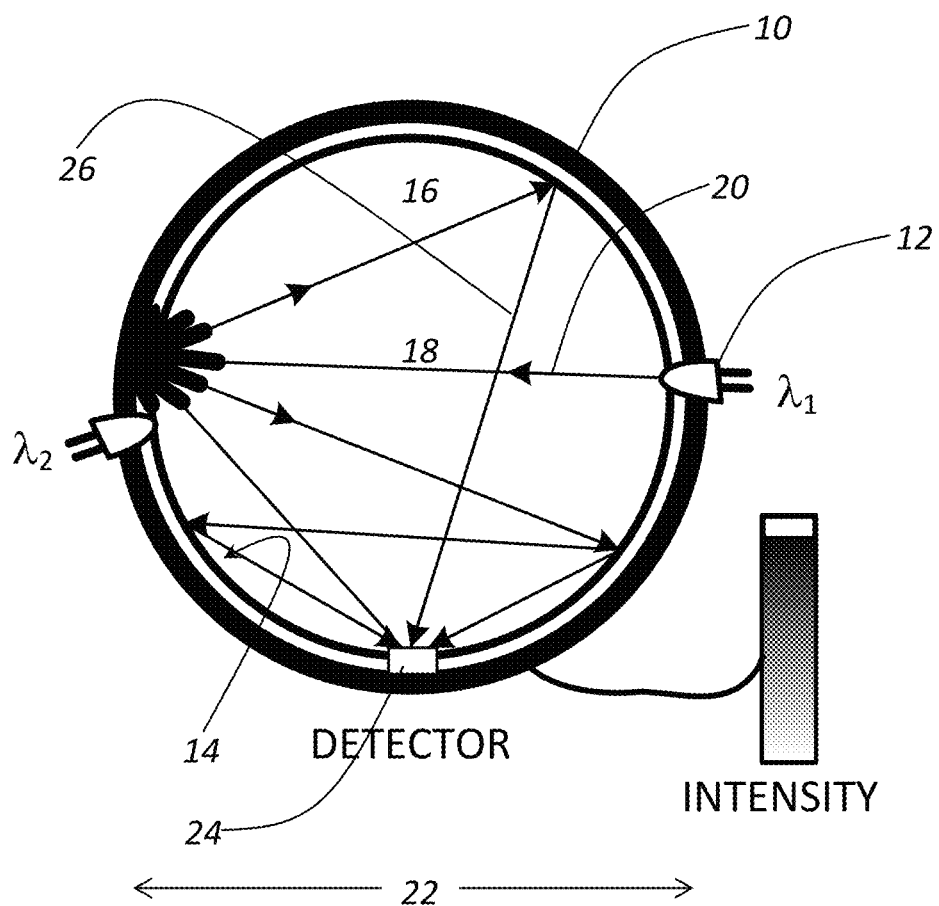
FIG. 1 is a schematic diagram illustrating one exemplary embodiment of the optical density monitor and comparator system of the present disclosure, containing a fluid sample to be quantified.

Referring now specifically to FIG. 1, again, in one exemplary embodiment, the present disclosure provides an integrating sphere or multi-pass cell (collectively referred to herein as a flow cell 10) including one or more UV LEDs or the like 12 disposed around and/or through the interior periphery 14 thereof. The one or more UV LEDs 12 are operable for irradiating the interior 16 of the flow cell 10, which contains and confines a fluid sample 18 in substantially the entire internal volume 16 of the flow cell 10, thereby maximizing path length 20 through the fluid sample 18. The path length 20 substantially coincides with the entire internal diameter 22 of the flow cell 10. One or more detectors 24 are also disposed at the interior periphery 14 of the flow cell 10, such that scattered radiation 26 within the interior 16 of the flow cell 10 impinges on and is detected by the one or more detectors 24.

The enhanced pathlength offered by integration spheres provides advantages in sensitivity. A 10-cm diameter integrating sphere results in a 250-cm pathlength, which is 250× that of a standard 1-cm cuvette. The increased pathlength inside the integrating sphere is a result of multiple reflections of the incoming radiation from the walls of the sphere which are typically made from a Lambertian scattering material. Each time the incoming radiation is reflected there is some attenuation of the signal which is affected by the reflectivity of the wall of the sphere as well as the absorption coefficient of the medium inside the sphere. A good approximation of the pathlength is determined by setting the Beer-Lambert law equal to the integrating sphere multiplier, M, which describes the increase in radiance in an integrating sphere due to multiple reflections.

Sphere Multiplier $$M = \frac{\varphi}{\varphi_0} = \frac{\rho(1-f)}{1-\rho(1-f)}$$

Where f is the port hole fraction in the sphere and $\rho$ is the reflectivity of the sphere wall and $\varphi$ and $\varphi_0$ are the internal radiance and initial radiance in the sphere, respectively.

Beer-Lambert $$\frac{\varphi}{\varphi_0} = e^{-\alpha z}$$

Where $\alpha$ is the absorption coefficient and z is the pathlength and $\varphi$ and $\varphi_0$ are the radiance with and without the presence of absorption, respectively.

The resulting effective pathlength, z, in an integrating sphere is defined by the following equation, which has been shown to have good agreement with experimental measurements:

$$z = \frac{-\ln\frac{\rho(1-f)}{1-\rho(1-f)}}{\alpha}$$

This effective increase in pathlength enables a higher level of sensitivity in the measurement because it maximizes the pathlength for both the irradiating source and the sample in a compact design. Because the sphere operates on the principle of multiple reflections, it is extremely sensitive to absorbing molecules.

One exemplary flow cell 10 is described in U.S. Patent Application Publication No. 2012/0318749 (commonly assigned). The flow cell 10 takes the form of an integrating sphere or the like. Although the integrating sphere configuration is discussed at length, other configurations may also be utilized. The key consideration is that photons are repeatedly reflected within the flow cell 10 and that a uniform radiation field is formed with low-intensity radiation sources. The flow cell 10 should have substantially curved and concave opposing interior surfaces, should not have internal corners, and every point on the interior surface of the flow cell 10 should be "visible" from every other point on the interior surface. Ovoids, ellipsoids, cubes with rounded corners, etc. all fit these criteria. The flow cell 10 is made of plastic or the like for ease of manufacturing, and, in such cases where the material is not a good Lambertian scatterer, the interior surfaces thereof are coated with a Lambertian scattering material. Alternatively, the flow cell 10 is made of a metallic or other reflective or coated reflective material, such as aluminum, stainless steel, copper, etc., which may be anodized or otherwise coated with organic polymer, silicone, inorganic oxide, etc. The flow cell 10 is scalable and may have any suitable dimensions, on the order of millimeters to meters, for example.

The flow cell 10 includes at least an inlet port (not illustrated) and an outlet port (not illustrated) manufactured into it that provides for the flow of the fluid sample 18 (i.e. a liquid or a gas) from the inlet port to the outlet port. Alternatively, the inlet port and the outlet port may consist of the sample port. It will be readily apparent to those of ordinary skill in the art that multiple inlet ports and/or multiple outlet ports may also be utilized.

In the nominal design, one or more point radiation sources 12, such as one or more UV optical sources, one or more deep-UV optical sources, one or more semiconductor optical sources, and/or one or more light-emitting diode (LED) optical sources, are disposed within or partially or wholly through one or more ports (not illustrated) manufactured through the flow cell 10, optionally at symmetrically-disposed positions. "Point radiation sources" as used herein, refer to small, roughly symmetrical radiation sources, as compared to the other dimensions of the system.

Referring again specifically to FIG. 1, one exemplary application of the present invention involves measuring the optical density of a water influent or effluent to a disinfection reactor or the like. The optical density of water in the UV region is important for determining the efficacy of water disinfection reactors that use UV radiation to inactivate organisms in the water. This practice is commonly referred to as measuring the UV transmission (UVT) of the water. In this implementation, one LED is used at 260 nm, for example, the typical wavelength used for water disinfection.

Another exemplary application of the present invention involves measuring nucleic acid concentrations in a sample and quantifying the ratio of nucleic acids to protein in solution. The present invention is significantly different from the current methods of sample measurement in that it allows the sample to fill the entirety of the interior of the integrating sphere 10, making the sphere the effective sample holder. This enables a higher level of sensitivity in the measurement because it maximizes the path length 20 for both the irradiating source 12 and the sample 18 in a compact design. Because the sphere 10 operates on the principle of multiple reflections, it is extremely sensitive to absorbing molecules. Two LED optical sources 12 are used in this implementation, for example, one at 260 nm, the peak of DNA absorbance, and one at 280 nm, the peak of protein absorbance.

Figure 2:
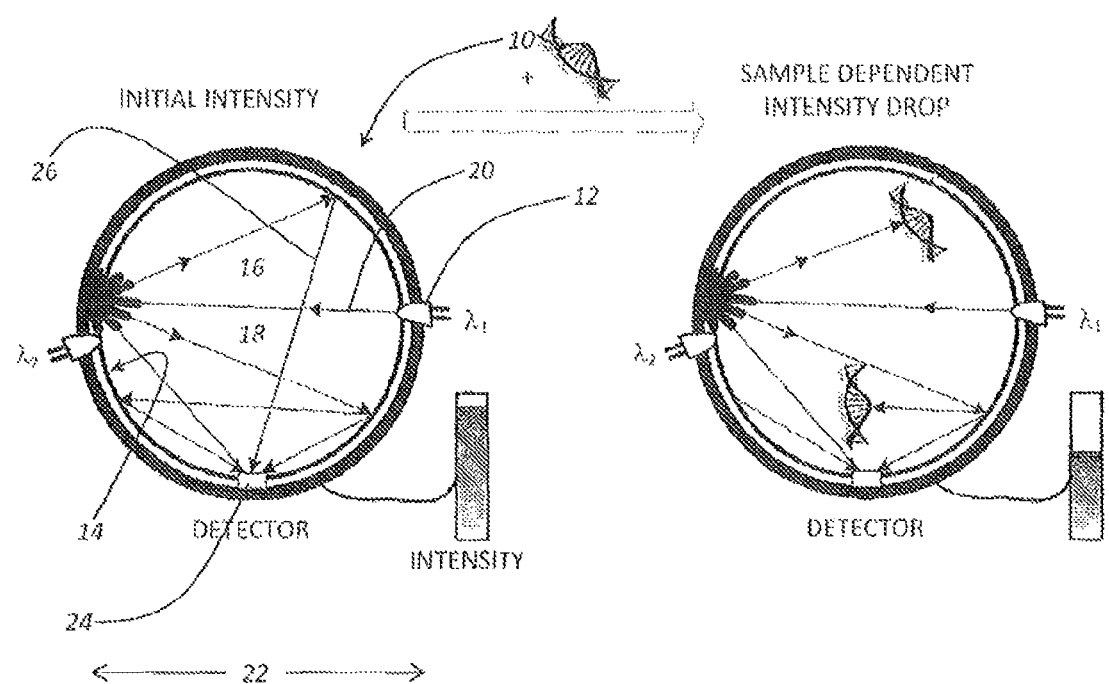
FIG. 2 is a schematic diagram illustrating one exemplary embodiment of the optical density monitor and comparator system of the present disclosure, containing a fluid sample and DNA/RNA or the like to be quantified.

Referring now specifically to FIG. 2, the system is used for such nucleic acid quantitation. On the left hand side a detector 24 on a porthole of the integrating sphere 10 measures a specific intensity at wavelength-1 and wavelength-2 (typically with 260 nm and 280 nm LED sources irradiating the interior 16 of the sphere 10, for example). The intensity at each wavelength drops with the addition of the sample 18 inside the sphere 10 (right-hand side) and the sensitivity to the sample absorption is increased due to the long path length 26 provided by the integrating sphere 10.

Figure 3:
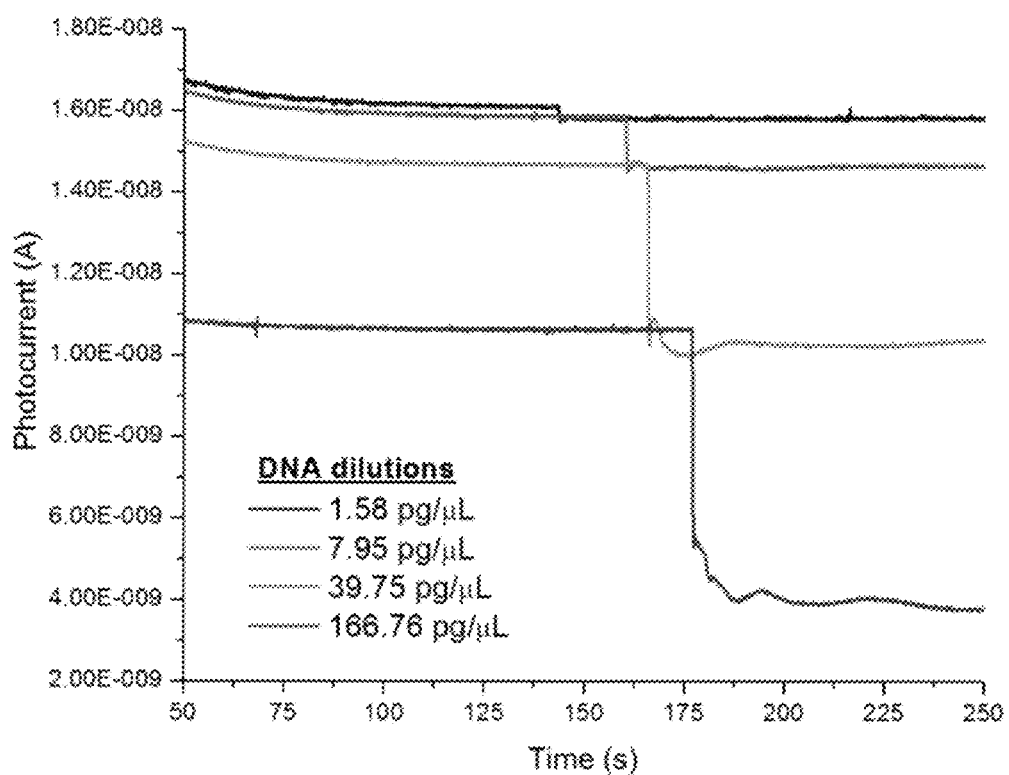
FIG. 3 is a plot illustrating photodiode response in a 4-inch integrating sphere with a 255-nm LED source to various DNA dilutions.

By increasing the absorption pathlength of a sample, the level of sensitivity of the measurement will also be increased; alternately, smaller sample volumes or more dilute samples can be used for measurement. This effect was seen in preliminary data taken using a custom four inch diameter integrating sphere made of virgin PTFE with a 96% surface reflectance in the ultraviolet wavelength range. The sphere was filled with deionized water and a 10 mW, 255 nm LED was used as the input radiation source. A SiC photodiode monitored the flux inside the integrating sphere. Herring sperm was inoculated in the integrating sphere at increasingly less dilute samples until an absorption response, seen as a drop in the photodiode current, was measured. As can be seen in FIG. 3, a response was measured at a DNA dilution of 1.58 pg/μL. Also, as less dilute samples were inoculated into the sphere the drop in photocurrent increased as was expected. The preliminary data showed a response at 1.58 pg/μL which is 1000× lower than other absorbance based nucleic acid quantitation systems.

Figure 4:
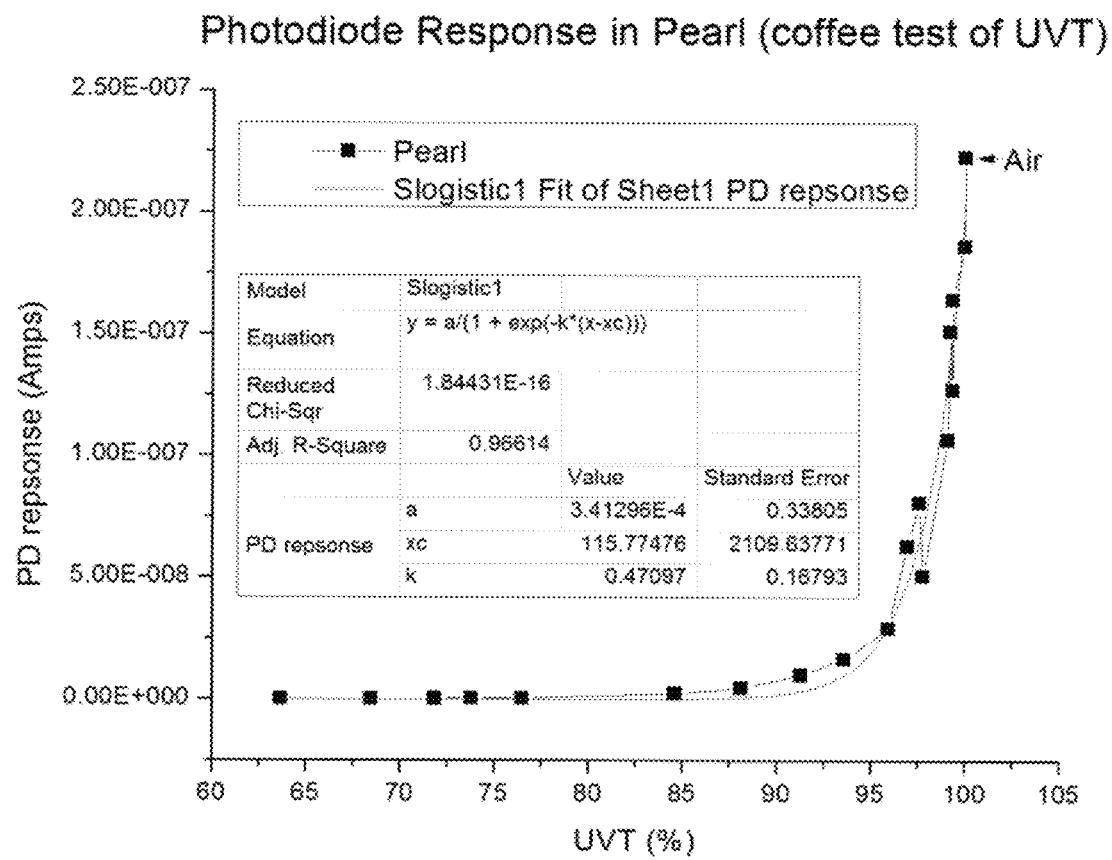
FIG. 4 is a plot illustrating photodiode response positioned in the side of a Beta Pearl reactor which was filled with air, distilled water, and distilled water combined with varying amounts of instant coffee to adjust the UV transmittance of the water.

The application of using the integrating sphere as an optical density monitor was also explored experimentally. Inside the sphere increasingly higher levels of coffee were added to water to adjust the UVT of the water. The photodiode response of a photodiode situated into the side of the sphere was measured and compared to 1-cm cuvette readings of the same liquid measured using a standard spectrophotometer (see FIG. 4). Large changes in the photodiode response were observed for very small changes in liquid UVT, indicating the sphere could be a very sensitive measurement tool for performing absorption based measurements on liquids contained in the sphere interior.

Although the present disclosure is illustrated and described herein with reference to preferred embodiments and specific examples thereof, it will be readily apparent to those of ordinary skill in the art that other embodiments and examples may perform similar functions and/or achieve like results. All such equivalent embodiments and examples are within the spirit and scope of the present disclosure, are contemplated thereby, and are intended to be covered by the following claims.

What is claimed is:

1. A system for determining the absorption coefficient and/or the optical density of a fluid and/or organic/inorganic particles disposed in the fluid, comprising:
    an integrating flow cell configured to contain a fluid sample within substantially an entire interior portion thereof;
    one or more point radiation sources disposed about an interior periphery of the integrating flow cell, wherein the one or more point radiation sources are operable for delivering radiation of a predetermined wavelength to the fluid sample; and
    one or more radiation detectors operable for detecting radiation within the interior portion of the integrating flow cell;
    wherein the integrating flow cell comprises an integrating sphere having an interior surface operable for reflecting the radiation delivered to the fluid sample by the one or more point radiation sources such that a radiation intensity is uniform throughout the interior portion of the flow cell; and
    wherein a path length of the radiation delivered to the fluid sample and reflected is maximized by the fluid sample occupying substantially the entire interior portion of the integrating flow cell.

2. The system of claim 1, wherein the absorption coefficient and/or the optical density of the fluid and/or organic/inorganic particles disposed in the fluid is determined utilizing the predetermined wavelength of the delivered radiation and a characteristic of the detected radiation.

3. The system of claim 1, wherein the determined absorption coefficient and/or optical density of the fluid and/or organic/inorganic particles disposed in the fluid is measured at one or more predetermined wavelengths of delivered radiation and a ratio of measured values is used to identify the fluid and/or organic/inorganic particles disposed in the fluid.

4. The system of claim 1, wherein the one or more point radiation sources comprise a first point radiation source operable for delivering radiation of a first predetermined wavelength to the fluid sample.

5. The system of claim 4, wherein the one or more point radiation sources further comprise a second point radiation source operable for delivering radiation of a second predetermined wavelength to the fluid sample.

6. The system of claim 1, wherein the one or more point radiation sources comprise one or more ultraviolet (UV) point radiation sources and/or one or more visible point radiation sources.

7. The system of claim 1, wherein the one or more point radiation sources comprise a point radiation source operable for delivering radiation having a predetermined wavelength of between about 260 nm and about 280 nm to the fluid sample.

8. The system of claim 1, wherein the one or more point radiation sources comprise one or more semiconductor optical sources, light-emitting diode (LED) optical sources, and ultraviolet (UV) optical sources.

9. A method for determining the absorption coefficient and/or the optical density of a fluid and/or organic/inorganic particles disposed in the fluid, comprising:
    providing an integrating flow cell configured to contain a fluid sample within substantially an entire interior portion thereof;
    providing one or more point radiation sources disposed about an interior periphery of the integrating flow cell, wherein the one or more point radiation sources are operable for delivering radiation of a predetermined wavelength to the fluid sample; and
    providing one or more radiation detectors operable for detecting radiation within the interior portion of the integrating flow cell;
    wherein the integrating flow cell comprises an integrating sphere having an interior surface operable for reflecting the radiation delivered to the fluid sample by the one or more point radiation sources such that a radiation intensity is uniform throughout the interior portion of the flow cell; and
    wherein a path length of the radiation delivered to the fluid sample and reflected is maximized by the fluid sample occupying substantially the entire interior portion of the integrating flow cell.

10. The method of claim 9, wherein the absorption coefficient and/or the optical density of the fluid and/or organic/inorganic particles disposed in the fluid is determined utilizing the predetermined wavelength of the delivered radiation and a characteristic of the detected radiation.

11. The method of claim 9, wherein the determined absorption coefficient and/or optical density of the fluid and/or organic/inorganic particles disposed in the fluid is measured at one or more predetermined wavelengths of delivered radiation and a ratio of measured values is used to identify the fluid and/or organic/inorganic particles disposed in the fluid.

12. The method of claim 9, wherein the one or more point radiation sources comprise a first point radiation source operable for delivering radiation of a first predetermined wavelength to the fluid sample.

13. The method of claim 12, wherein the one or more point radiation sources further comprise a second point radiation source operable for delivering radiation of a second predetermined wavelength to the fluid sample.

14. The method of claim 9, wherein the one or more point radiation sources comprise one or more ultraviolet (UV) point radiation sources and/or one or more visible point radiation sources.

15. The method of claim 9, wherein the one or more point radiation sources comprise a point radiation source operable for delivering radiation having a predetermined wavelength of between about 260 nm and about 280 nm to the fluid sample.

16. The method of claim 9, wherein the one or more point radiation sources comprise one or more semiconductor optical sources, light-emitting diode (LED) optical sources, and ultraviolet (UV) optical source.

* * * * *